US008083766B2

(12) United States Patent
McGuckin, Jr.

(10) Patent No.: US 8,083,766 B2
(45) Date of Patent: Dec. 27, 2011

(54) SEPTAL DEFECT CLOSURE DEVICE

(75) Inventor: James F. McGuckin, Jr., Radnor, PA (US)

(73) Assignee: Rex Medical, LP, Conshohocken, PA (US)

(*) Notice: Subject to any disclaimer, the term of this patent is extended or adjusted under 35 U.S.C. 154(b) by 343 days.

(21) Appl. No.: 11/482,317

(22) Filed: Jul. 7, 2006

(65) Prior Publication Data
US 2006/0276839 A1    Dec. 7, 2006

Related U.S. Application Data

(63) Continuation-in-part of application No. 10/847,141, filed on May 17, 2004, now Pat. No. 7,662,161, which is a continuation-in-part of application No. 10/345,533, filed on Jan. 16, 2003, now Pat. No. 7,267,679, which is a continuation-in-part of application No. 10/163,142, filed on Jun. 5, 2002, now Pat. No. 7,341,595, which is a continuation-in-part of application No. 09/659,648, filed on Sep. 12, 2000, now abandoned.

(60) Provisional application No. 60/355,526, filed on Feb. 6, 2002, provisional application No. 60/153,736, filed on Sep. 13, 1999.

(51) Int. Cl.
*A61B 17/08* (2006.01)
*A61D 1/00* (2006.01)
(52) U.S. Cl. ............................................ 606/213
(58) Field of Classification Search ........... 606/151–154, 606/157, 213, 215, 216, 218–221
See application file for complete search history.

(56) References Cited

U.S. PATENT DOCUMENTS

| 2,024,871 A | 12/1935 | Parsons |
| 2,398,220 A | 2/1946 | Gelpcke |
| 3,527,223 A | 9/1970 | Shein |
| 3,874,388 A | 4/1975 | King et al. |
| 3,937,217 A | 2/1976 | Kosonen |
| 3,958,576 A | 5/1976 | Komiya |
| 4,007,743 A | 2/1977 | Blake |
| 4,031,569 A | 6/1977 | Jacob |
| 4,117,838 A | 10/1978 | Hasson |
| 4,286,497 A | 9/1981 | Shamah |
| 4,317,445 A | 3/1982 | Robinson |
| 4,485,816 A | 12/1984 | Krumme |
| 4,505,274 A | 3/1985 | Speelman |
| 4,512,338 A | 4/1985 | Balko et al. |
| 4,610,671 A | 9/1986 | Luther |
| 4,615,514 A | 10/1986 | Hamlin |
| 4,638,803 A * | 1/1987 | Rand ............................ 606/192 |

(Continued)

FOREIGN PATENT DOCUMENTS
DE    19604817    8/1997

(Continued)

*Primary Examiner* — Corrine M McDermott
*Assistant Examiner* — Dianne Dornbusch
(74) *Attorney, Agent, or Firm* — Neil D. Gershon

(57) ABSTRACT

A device for closing a septal defect of a patient comprising a covering member and at least one retaining leg. The covering member has a first configuration for delivery and a second configuration for placement on the first side of the defect. The at least one retaining leg is configured to contact tissue on the second side of the defect to retain the covering member and has a first configuration for delivery and a second configuration for placement on the second side of the defect.

15 Claims, 8 Drawing Sheets

U.S. PATENT DOCUMENTS

| | | | |
|---|---|---|---|
| 4,665,906 A | 5/1987 | Jervis | |
| 4,676,245 A | 6/1987 | Eukuda | |
| 4,744,364 A | 5/1988 | Kensey | |
| 4,836,204 A * | 6/1989 | Landymore et al. | 606/215 |
| 4,917,089 A | 4/1990 | Sideris | |
| 4,924,866 A | 5/1990 | Yoon | |
| 4,971,068 A | 11/1990 | Sahi | |
| 5,021,059 A | 6/1991 | Kensey et al. | |
| 5,047,047 A | 9/1991 | Yoon | |
| 5,061,274 A | 10/1991 | Kensey | |
| 5,108,420 A * | 4/1992 | Marks | 606/213 |
| 5,171,252 A | 12/1992 | Friedland | |
| 5,171,259 A | 12/1992 | Inoue | |
| 5,192,300 A | 3/1993 | Fowler | |
| 5,192,301 A | 3/1993 | Kamilya et al. | |
| 5,192,302 A | 3/1993 | Kensey et al. | |
| 5,222,974 A | 6/1993 | Kensey et al. | |
| 5,246,441 A | 9/1993 | Ross et al. | |
| 5,279,572 A | 1/1994 | Hokama | |
| 5,282,827 A | 2/1994 | Kensey et al. | |
| 5,306,254 A | 4/1994 | Nash et al. | |
| 5,312,435 A | 5/1994 | Nash et al. | |
| 5,334,210 A * | 8/1994 | Gianturco | 606/151 |
| 5,350,399 A | 9/1994 | Erlebacher et al. | |
| 5,350,400 A | 9/1994 | Esposito et al. | |
| 5,385,554 A | 1/1995 | Brimhall | |
| RE34,866 E | 2/1995 | Kensey et al. | |
| 5,391,183 A | 2/1995 | Janzen et al. | |
| 5,411,520 A | 5/1995 | Nash et al. | |
| 5,425,744 A | 6/1995 | Fagan et al. | |
| 5,443,481 A | 8/1995 | Lee | |
| 5,451,235 A | 9/1995 | Lock et al. | |
| 5,474,557 A | 12/1995 | Mai | |
| 5,478,352 A | 12/1995 | Fowler | |
| 5,478,353 A | 12/1995 | Yoon | |
| 5,486,195 A | 1/1996 | Myers et al. | |
| 5,531,759 A | 7/1996 | Kensey et al. | |
| 5,540,716 A | 7/1996 | Hlavacek | |
| 5,545,178 A | 8/1996 | Kensey et al. | |
| 5,549,633 A | 8/1996 | Evans et al. | |
| 5,591,204 A | 1/1997 | Janzen et al. | |
| 5,593,422 A | 1/1997 | Muijs Van de Moer et al. | |
| 5,620,461 A | 4/1997 | Muijs Van de Moer et al. | |
| 5,630,833 A | 5/1997 | Katsaros et al. | |
| 5,634,936 A * | 6/1997 | Linden et al. | 606/213 |
| 5,643,317 A | 7/1997 | Pavcnik et al. | |
| 5,649,959 A | 7/1997 | Hannam et al. | |
| 5,662,681 A | 9/1997 | Nash et al. | |
| 5,674,231 A | 10/1997 | Green et al. | |
| 5,676,689 A | 10/1997 | Kensey et al. | |
| 5,690,674 A | 11/1997 | Diaz | |
| 5,700,277 A | 12/1997 | Nash et al. | |
| 5,702,421 A | 12/1997 | Schneidt | |
| 5,709,707 A | 1/1998 | Lock et al. | |
| 5,725,498 A | 3/1998 | Janzen et al. | |
| 5,725,552 A | 3/1998 | Kotula et al. | |
| 5,728,132 A | 3/1998 | Van Tassel et al. | |
| 5,728,133 A | 3/1998 | Kontos | |
| 5,741,297 A | 4/1998 | Simon | |
| 5,776,162 A | 7/1998 | Kleshinski | |
| 5,782,860 A | 7/1998 | Epstein et al. | |
| 5,782,861 A | 7/1998 | Cragg et al. | |
| 5,810,846 A | 9/1998 | Virnich et al. | |
| 5,810,884 A | 9/1998 | Kim | |
| 5,820,628 A | 10/1998 | Middleman et al. | |
| 5,836,968 A | 11/1998 | Simon et al. | |
| 5,846,261 A | 12/1998 | Kotula et al. | |
| 5,861,003 A * | 1/1999 | Latson et al. | 606/213 |
| 5,893,856 A | 4/1999 | Jacob et al. | |
| 5,902,317 A | 5/1999 | Kleshinski et al. | |
| 5,904,703 A | 5/1999 | Gilson | |
| 5,910,155 A | 6/1999 | Ratcliff et al. | |
| 5,916,235 A * | 6/1999 | Guglielmi | 606/200 |
| 5,916,236 A | 6/1999 | Muijs Van de Moer et al. | |
| 5,919,207 A | 7/1999 | Taheri | |
| 5,944,738 A | 8/1999 | Amplatz et al. | |
| 5,964,782 A | 10/1999 | Lafontaine et al. | |
| 5,976,159 A | 11/1999 | Bolduc et al. | |
| 5,976,174 A * | 11/1999 | Ruiz | 606/213 |
| 5,984,949 A | 11/1999 | Levin | |
| 6,001,110 A | 12/1999 | Adams | |
| 6,007,558 A | 12/1999 | Ravenscroft et al. | |
| 6,007,563 A | 12/1999 | Nash et al. | |
| 6,010,517 A * | 1/2000 | Baccaro | 606/151 |
| 6,015,417 A | 1/2000 | Reynolds | |
| 6,033,427 A | 3/2000 | Lee | |
| 6,048,357 A | 4/2000 | Kontos | |
| 6,048,358 A | 4/2000 | Barak | |
| 6,056,768 A | 5/2000 | Cates et al. | |
| 6,063,085 A | 5/2000 | Tay et al. | |
| 6,071,300 A | 6/2000 | Brenneman et al. | |
| 6,077,281 A | 6/2000 | Das | |
| 6,080,182 A | 6/2000 | Shaw et al. | |
| 6,080,183 A | 6/2000 | Tsugita et al. | |
| 6,113,611 A | 9/2000 | Allen et al. | |
| 6,117,159 A | 9/2000 | Heubsch et al. | |
| 6,120,524 A | 9/2000 | Taheri | |
| 6,139,564 A | 10/2000 | Teoh | |
| 6,171,320 B1 | 1/2001 | Monassevitch | |
| 6,171,329 B1 | 1/2001 | Shaw et al. | |
| 6,174,322 B1 | 1/2001 | Schneidt | |
| 6,179,863 B1 | 1/2001 | Kensey | |
| 6,187,040 B1 | 2/2001 | Wright | |
| 6,193,708 B1 * | 2/2001 | Ken et al. | 606/1 |
| 6,197,042 B1 | 3/2001 | Ginn et al. | |
| 6,206,907 B1 | 3/2001 | Marino et al. | |
| 6,214,029 B1 | 4/2001 | Thill et al. | |
| 6,228,096 B1 | 5/2001 | Marchand | |
| 6,231,561 B1 | 5/2001 | Frazier et al. | |
| 6,231,602 B1 | 5/2001 | Carpentier et al. | |
| 6,250,308 B1 | 6/2001 | Cox | |
| 6,251,122 B1 | 6/2001 | Tsukernik | |
| 6,258,026 B1 | 7/2001 | Ravenscroft et al. | |
| 6,258,120 B1 | 7/2001 | McKenzie et al. | |
| 6,261,309 B1 | 7/2001 | Urbanski | |
| 6,270,515 B1 * | 8/2001 | Linden et al. | 606/213 |
| 6,277,140 B2 | 8/2001 | Ginn et al. | |
| 6,328,727 B1 | 12/2001 | Frazier et al. | |
| 6,334,865 B1 | 1/2002 | Redmond et al. | |
| 6,336,914 B1 | 1/2002 | Gillespie | |
| 6,342,064 B1 | 1/2002 | Koike et al. | |
| 6,346,117 B1 * | 2/2002 | Greenhalgh | 606/200 |
| 6,350,270 B1 * | 2/2002 | Roue | 606/151 |
| 6,350,274 B1 | 2/2002 | Li | |
| 6,355,052 B1 | 3/2002 | Neuss | |
| 6,368,341 B1 | 4/2002 | Abrahamson | |
| 6,391,037 B1 * | 5/2002 | Greenhalgh | 606/151 |
| 6,391,048 B1 | 5/2002 | Ginn et al. | |
| 6,409,739 B1 | 6/2002 | Nobels et al. | |
| 6,419,669 B1 | 7/2002 | Frazier et al. | |
| 6,425,911 B1 | 7/2002 | Akerfeldt et al. | |
| 6,436,088 B2 | 8/2002 | Frazier et al. | |
| 6,440,152 B1 | 8/2002 | Gainor et al. | |
| 6,447,524 B1 | 9/2002 | Knodel et al. | |
| 6,461,366 B1 | 10/2002 | Seguin | |
| 6,482,179 B1 | 11/2002 | Chu et al. | |
| 6,508,828 B1 | 1/2003 | Akerfeldt et al. | |
| 6,537,299 B1 | 3/2003 | Hogendijk et al. | |
| 6,551,344 B2 | 4/2003 | Thill | |
| 6,569,185 B2 | 5/2003 | Ungs | |
| 6,585,748 B1 * | 7/2003 | Jeffree | 606/200 |
| 6,596,012 B2 | 7/2003 | Akerfeldt et al. | |
| 6,626,937 B1 | 9/2003 | Cox | |
| 6,645,225 B1 | 11/2003 | Atkinson | |
| 6,682,489 B2 | 1/2004 | Tenerz et al. | |
| 6,712,836 B1 | 3/2004 | Berg et al. | |
| 6,712,837 B2 | 3/2004 | Akerfeldt et al. | |
| 6,749,621 B2 | 6/2004 | Pantages et al. | |
| 6,752,813 B2 | 6/2004 | Goldfarb et al. | |
| 6,766,186 B1 | 7/2004 | Hoyns et al. | |
| 6,790,220 B2 | 9/2004 | Morris | |
| 6,846,316 B2 * | 1/2005 | Abrams | 606/200 |
| 6,855,153 B2 * | 2/2005 | Saadat | 606/194 |
| 6,911,037 B2 | 6/2005 | Gainor et al. | |
| 6,960,224 B2 | 11/2005 | Marino et al. | |
| 7,025,776 B1 | 4/2006 | Houser et al. | |
| 7,033,393 B2 | 4/2006 | Gainor et al. | |

| | | | | | |
|---|---|---|---|---|---|
| 7,153,323 B1 * | 12/2006 | Teoh et al. ............... 623/1.23 | 2005/0267524 A1 | 12/2005 | Chanduszko |
| 2002/0082622 A1 | 6/2002 | Kane | 2006/0069408 A1 | 3/2006 | Kato |
| 2002/0165572 A1 * | 11/2002 | Saadat ..................... 606/194 | 2006/0106418 A1 | 5/2006 | Seibold et al. |
| 2003/0055451 A1 * | 3/2003 | Jones et al. ............... 606/200 | 2006/0155327 A1 | 7/2006 | Briganti et al. |
| 2003/0088269 A1 | 5/2003 | Ashby | | | |
| 2003/0105487 A1 | 6/2003 | Bemz et al. | FOREIGN PATENT DOCUMENTS | | |
| 2003/0187473 A1 * | 10/2003 | Berenstein et al. ........ 606/200 | EP | 0637431 | 2/1995 |
| 2004/0002764 A1 | 1/2004 | Gainor et al. | EP | 0920842 | 6/1999 |
| 2004/0143294 A1 | 7/2004 | Corcoran et al. | WO | 9520916 | 8/1995 |
| 2004/0158287 A1 | 8/2004 | Cragg et al. | WO | 9707741 | 3/1997 |
| 2005/0033326 A1 | 2/2005 | Briganti et al. | WO | 9827868 | 7/1998 |
| 2005/0043759 A1 | 2/2005 | Chanduszko | WO | 9900055 | 1/1999 |
| 2005/0065547 A1 | 3/2005 | Marino et al. | WO | 9905977 | 2/1999 |
| 2005/0070957 A1 | 3/2005 | Das | WO | 9938454 | 8/1999 |
| 2005/0085852 A1 | 4/2005 | Ditter | WO | 2004012601 | 2/2004 |
| 2005/0090859 A1 | 4/2005 | Ravlkumar | WO | 2004112864 | 12/2004 |
| 2005/0107807 A1 | 5/2005 | Nakao | | | |
| 2005/0192627 A1 | 9/2005 | Whisenant et al. | * cited by examiner | | |

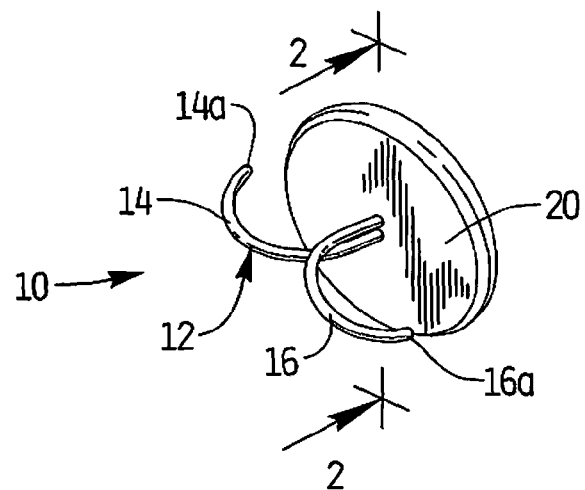
FIG_1
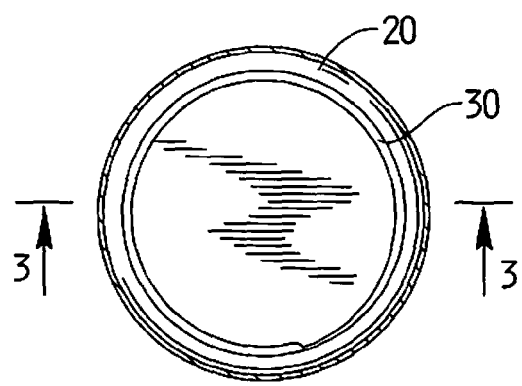
FIG_2
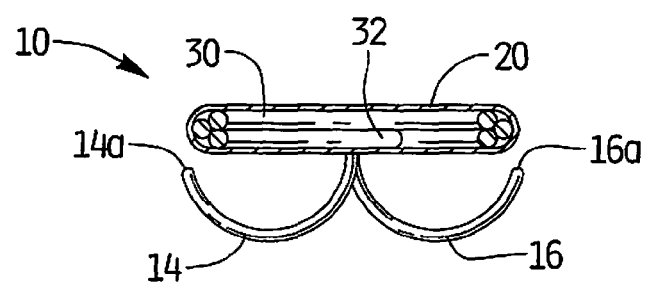
FIG_3

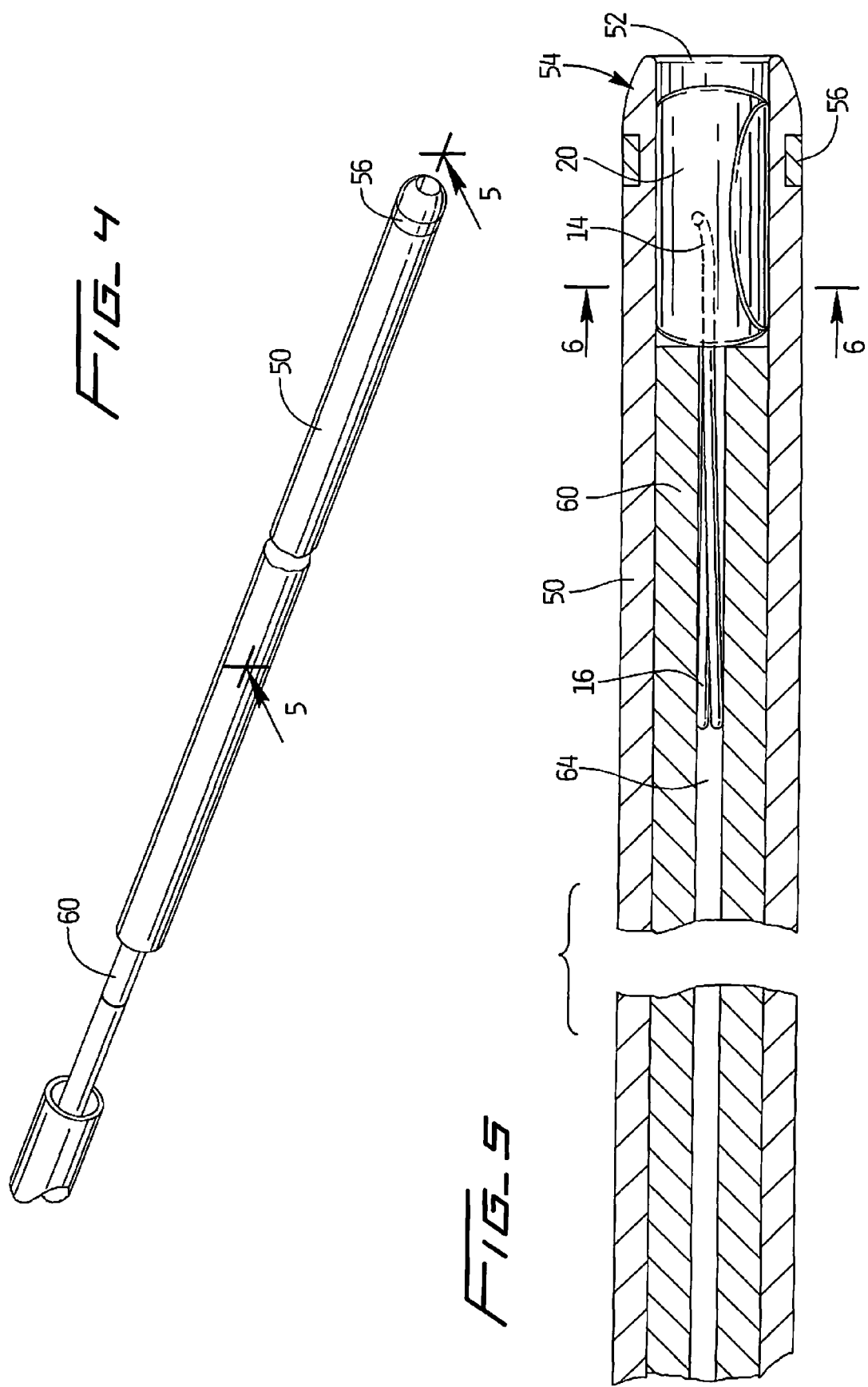

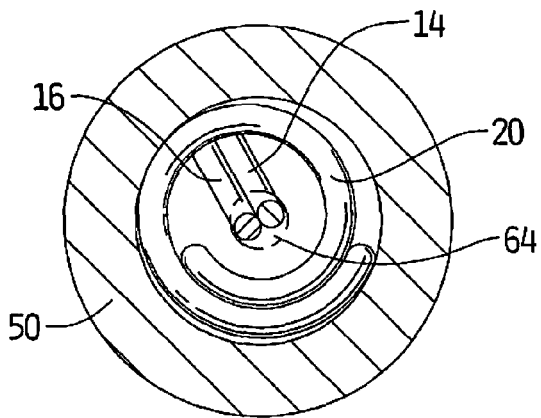
FIG_6
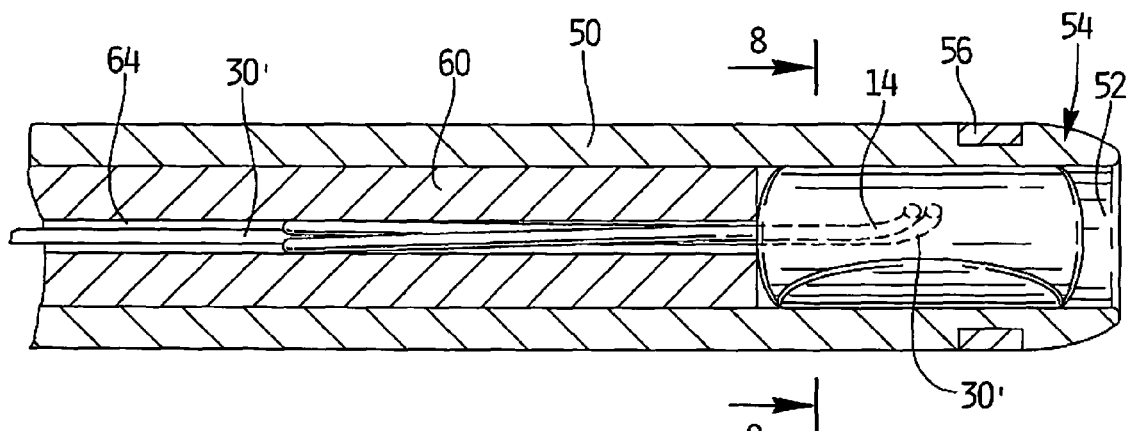
FIG_7
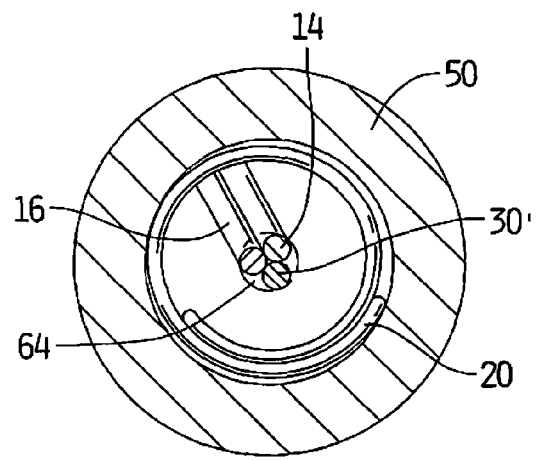
FIG_8

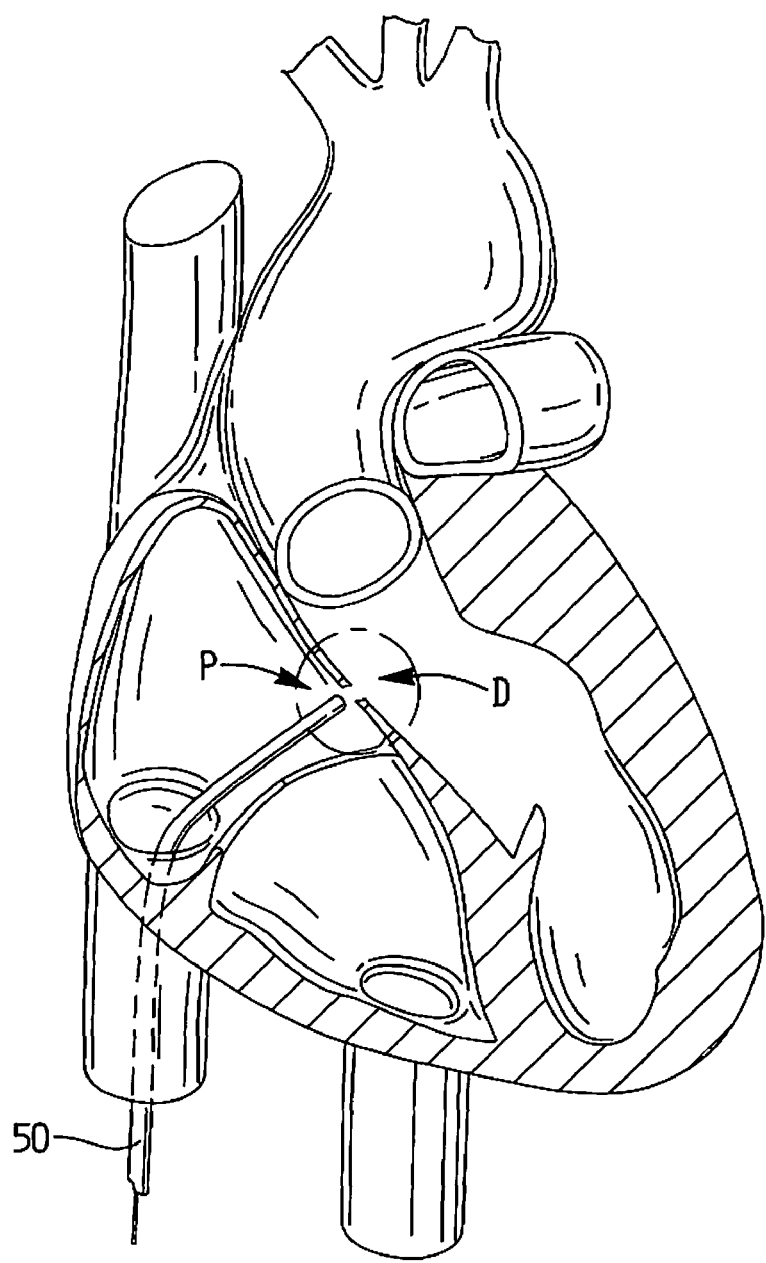
FIG_9

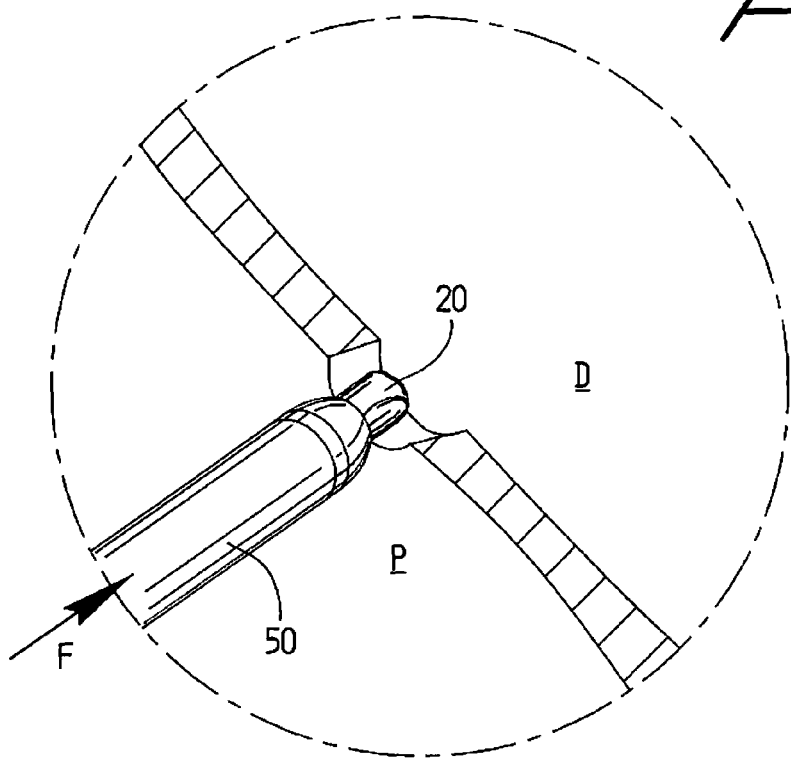
FIG_10
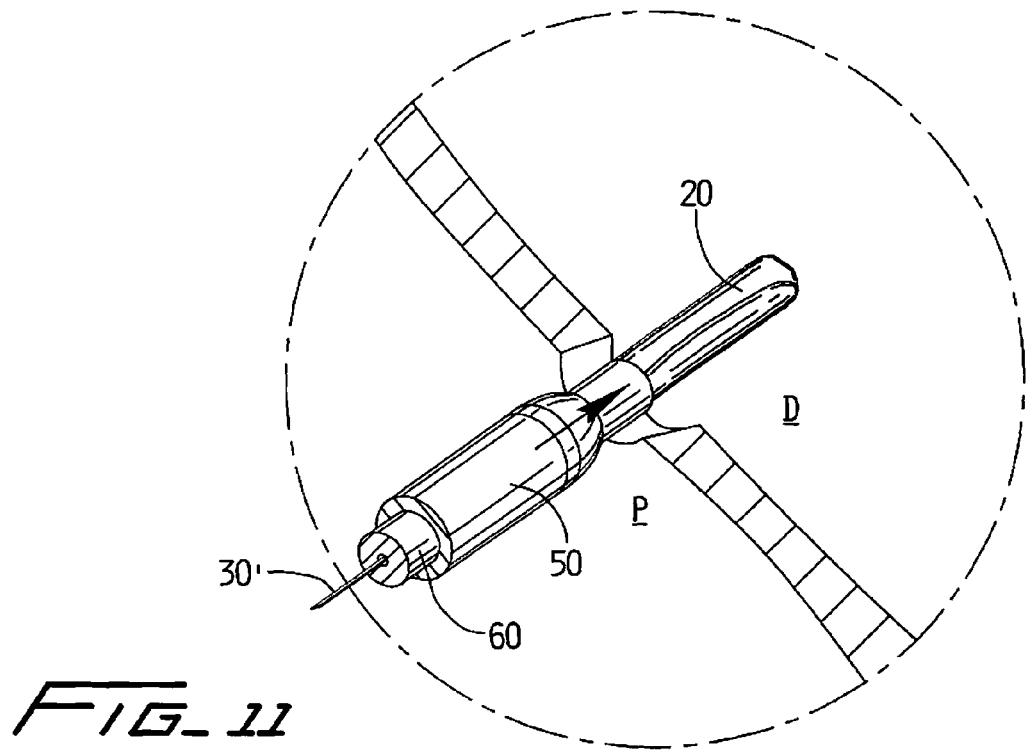
FIG_11

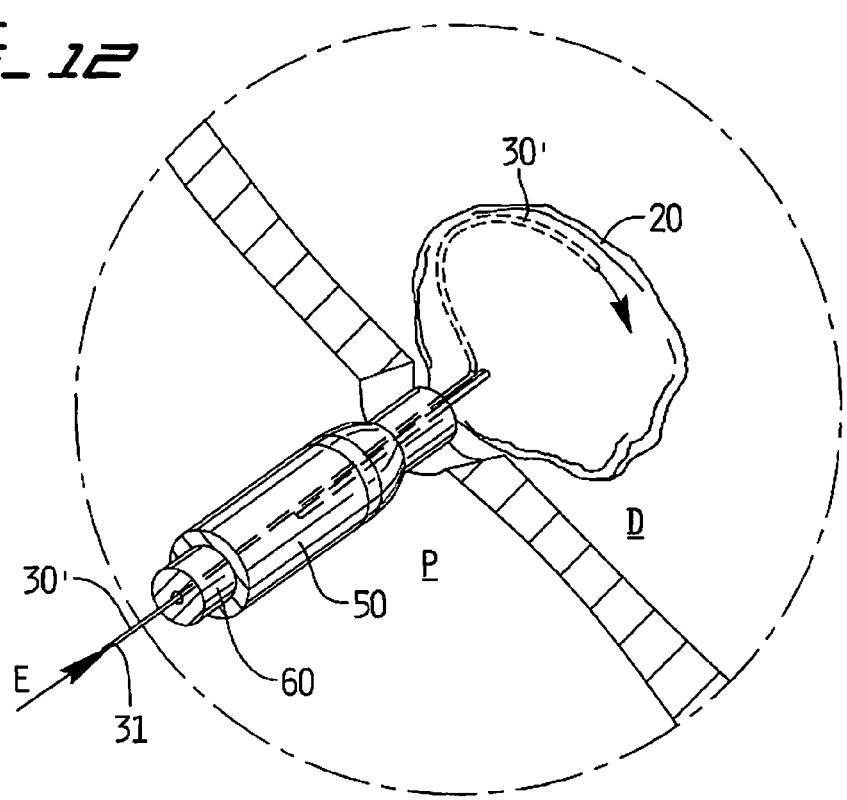
FIG_12
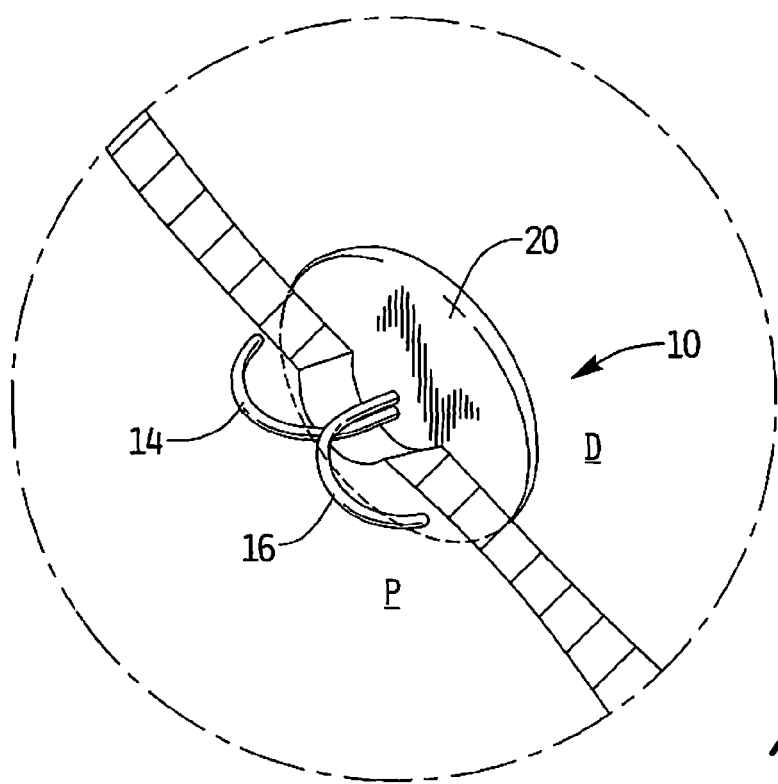
FIG_13

FIG_14
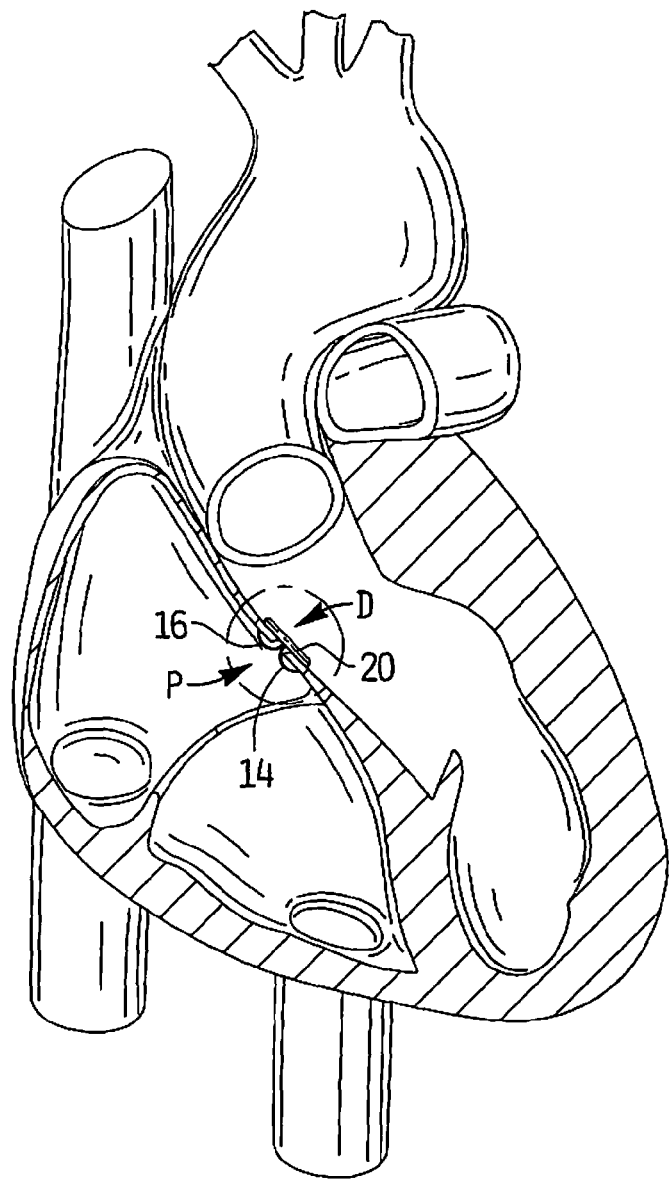
FIG_15
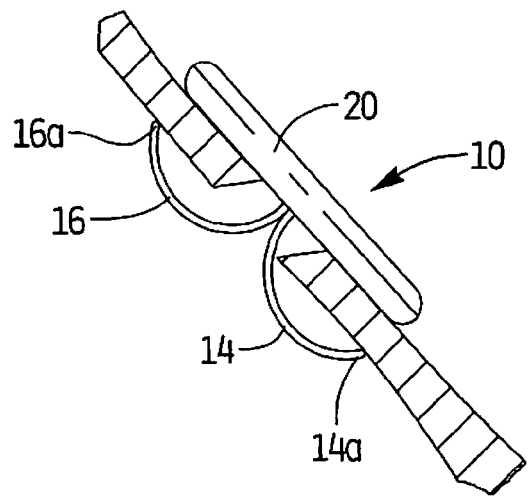

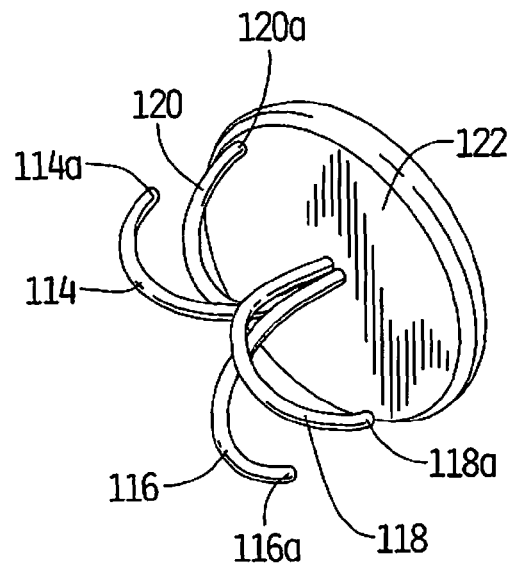
FIG_16
FIG_17
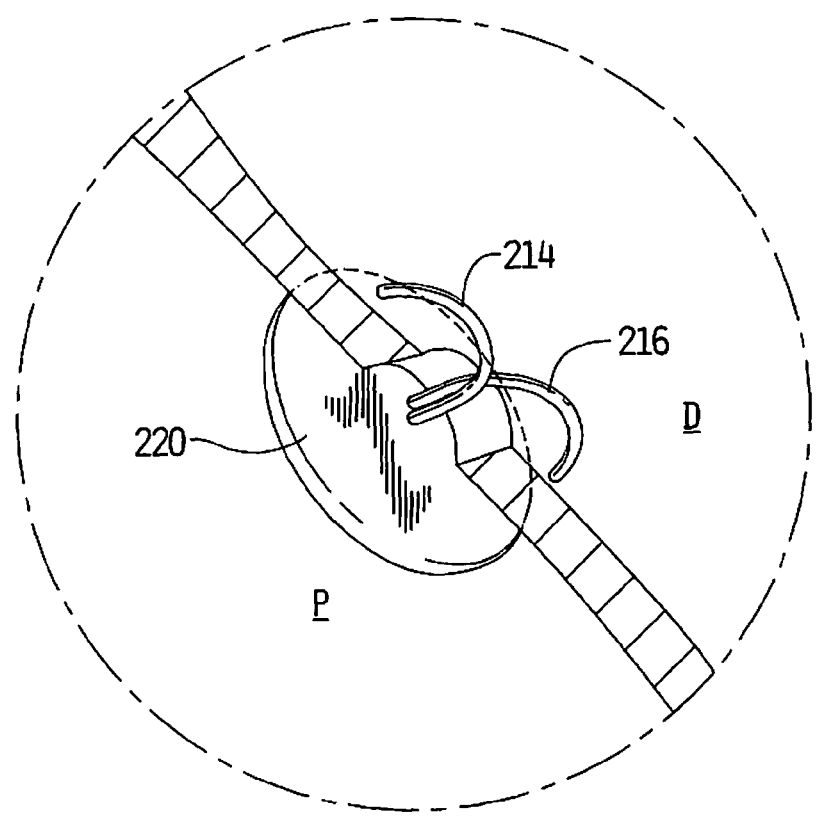

SEPTAL DEFECT CLOSURE DEVICE

This application is a continuation-in-part of U.S. patent application Ser. No. 10/847,141, filed May 17, 2004, now U.S. Pat. No. 7,662,161, which is a continuation-in-part of application Ser. No. 10/345,533, filed Jan. 16, 2003, now U.S. Pat. No. 7,267,679, which is a continuation-in-part of application Ser. No. 10/163,142, filed Jun. 5, 2002, now U.S. Pat. No. 7,341,595, which claims priority from provisional application Ser. No. 60/355,526, filed Feb. 6, 2002, and which is a continuation-in-part of application Ser. No. 09/659,648, filed Sep. 12, 2000 now abandoned, which claims priority from provisional patent application Ser. No. 60/153,736, filed Sep. 13, 1999. The contents of each of these applications are incorporated herein by reference in their entirety.

BACKGROUND

1. Technical Field

This application relates to a closure device and more particularly to a device for closing septal defects such as the patent foramen ovale.

2. Background of Related Art

Septal defects are perforations in the septum, a wall dividing two cavities, such as the atria of the heart. A trial defects can occur congenitally (by birth) or develop later such as after a heart attack.

One type of atrial defect is the foramen ovale. The foramen ovale is a valve-like opening between the two atria of the heart in the fetus. In most cases, it closes shortly before or after birth as fibrous tissue growth seals the opening. However, in some cases, the opening (defect) remains open (patent), allowing blood to shunt across the defect from the left atrium to the right atrium. This means that the un-oxygenated blood flows directly from the right side to the left side of the heart, where it travels through the aorta to the brain and other parts of the body. This can lead to life-threatening strokes as clots can travel to the brain. Additionally, since blood shunts from the higher pressure left ventricle into the lower pressure right side heart chambers and pulmonary arteries, this increase in flow at the high pressure can cause cardiac failure and even death.

One approach to treatment to prevent travel of the life-threatening blood clots is the administration of medications to break up the blood clots. However, these blood thinning medications are expensive, increase the risk of bleeding and could have adverse side effects. Another approach is to perform invasive open heart surgery to close off the patent foramen ovale (PFO) by suturing the tissue to close the opening or by suturing a patch to cover the defect. Such invasive open heart surgery is time consuming, traumatic to the patient, increases patient risk and recovery time, and increases costs as extended hospital stays are required.

It is therefore recognized that a minimally invasive approach to closing the septal defect to prevent the aforementioned migration of blood clots into cranial circulation and prevent cardiac overwork by high pressure flow would be beneficial. These devices, however, need to meet several criteria.

Such minimally invasive devices need to be collapsible to a small enough dimension to enable delivery through a small incision while being expandable to a sufficiently large dimension with sufficient stability to ensure sealing of the septal defect. The smaller the profile when collapsed the better the access and insertion. Providing a low profile once positioned is also advantageous because it minimizes disruption of blood flow.

There have been several attempts in the prior art to provide minimally invasive devices for closing a PFO. For example, in U.S. Pat. No. 5,846,261, a tubular wire braid of shape memory metal fabric is placed in the opening. In U.S. Pat. No. 5,944,738, two discs of braided shape memory wires are utilized. In U.S. Pat. No. 5,425,744, two Dacron covered shape memory frameworks are connected by a wire. In U.S. Pat. No. 5,861,003, two sacs of porous material supported by a wire frame are placed on opposing sides of the opening. In U.S. Pat. No. 6,712,836, a shape memory frame with fingers on both sides of the aperture to hold the plugging structure made of cloth or Dacron which extends through the aperture is disclosed.

It would be advantageous however to provide a device which provides stability to maintain the device position. It would also be advantageous to provide a device which presents a lower implantation profile as well as a lower insertion profile. This would minimize the insertion profile, facilitate passage to and through the defect, and provide less interference with blood flow.

Commonly assigned U.S. patent Ser. No. 10/847,141, filed May 17, 2004, discloses a device for closing vessel apertures. The present application provides a closure device with a reduced profile internally supported patch adapted for closing septal defects such as the patent foramen ovale.

SUMMARY

The present invention overcomes the problems and deficiencies of the prior art. The present invention provides a device for closing a septal defect of a patient. The device comprises a covering member and at least one retaining leg. The covering member has a first configuration for delivery and a second larger configuration for placement on a first side of the defect. The covering member has a dimension at least equal to the size of the defect to cover the defect. The at least one retaining leg is configured to contact tissue on a second side of the defect to retain the covering member and has a first reduced profile configuration for delivery and a second configuration for placement on the second side of the defect.

In a preferred embodiment, the covering member includes a support in the form of a wire composed of shape memory material and is substantially ring or disc-shaped in the second configuration wherein movement of the support to the second configuration expands the covering member. In a preferred embodiment, the at least one retaining leg is composed of shape memory material. In one embodiment, the at least one retaining leg comprises two legs, wherein in the second configuration the two legs curve radially outwardly in different directions to engage tissue on the second side of the defect. In an alternate embodiment, the at least one retaining leg comprises four legs.

In a preferred embodiment, the covering member is placed on a distal side of the defect and the at least one retaining leg is placed on a proximal side of the defect.

The present invention also provides a method of closing a septal defect comprising:

providing a covering member for delivery to a distal side of the septal defect, the covering member having a dimension at least equal to a size of the defect to cover the defect;

delivering the covering member in a collapsed position to the distal side of the septal defect, the covering member moving to a placement configuration to cover the distal side of the defect; and delivering at least one retaining member in an elongated position to a proximal side of the defect, the retaining member moving to a curved position to engage tissue on the proximal side of the defect to retain the covering member on the distal side of the defect.

In one embodiment, the step of delivering the covering member occurs prior to the expansion of the covering member. In another embodiment, the covering member has an expandable wire positioned therein composed of shape memory material so that upon delivery the wire expands to expand the covering member to the placement configuration. In a preferred embodiment, the at least one retaining member is composed of shape memory material so that upon delivery, the retaining member automatically moves to a curved placement position. In a preferred embodiment, the at least one retaining member comprises first and second legs.

BRIEF DESCRIPTION OF THE DRAWINGS

Preferred embodiment(s) of the present disclosure are described herein with reference to the drawings wherein:

FIG. 1 is a perspective view of a first embodiment of the closure device of the present invention shown in the placement configuration;

FIG. 2 is a bottom view of the closure device of FIG. 1;

FIG. 3 is a side view of the closure device of FIG. 1;

FIG. 4 is a perspective view of a delivery instrument for delivering the closure device of FIG. 1 to the surgical site;

FIG. 5 is a longitudinal cross-sectional view taken along line 5-5 of FIG. 4 showing the closure device in the collapsed position within the delivery tube for delivery to the surgical site, the expanding wire positioned within the covering member;

FIG. 6 is a transverse cross-sectional view taken along line 6-6 of FIG. 5;

FIG. 7 is a longitudinal cross-sectional view similar to FIG. 5 showing an alternate method of delivering the closure device wherein in the collapsed position of the closure device, the expanding wire is positioned mostly outside the covering member for later advancement into the covering member;

FIG. 8 is a transverse cross-sectional view taken along line 8-8 of FIG. 7;

FIGS. 9-12 illustrate the method of delivering the closure device to the atria to repair a septal defect wherein FIG. 9 illustrates the delivery catheter inserted via a femoral approach to access the septal defect, the catheter extending from the femoral artery to a position adjacent the septal defect between the atria of the heart;

FIG. 10 is an enlarged view of the area of detail in FIG. 9 showing the covering member starting to be inserted through the defect;

FIG. 11 is a view similar to FIG. 10 showing further advancement of the covering member from the delivery device by distal advancement of the pusher in the direction of the arrow;

FIG. 12 is a view similar to FIG. 11 showing full advancement of the covering member from the delivery device and partial advancement of the wire into the covering member to expand the covering member;

FIG. 13 is a perspective view in the same area of detail of FIG. 12 illustrating the closure device fully deployed to close the septal defect;

FIG. 14 illustrates the anatomical placement of the closure device of FIG. 13 in the septal defect between the atria of the heart;

FIG. 15 is an enlarged view of the area detailed in FIG. 14 to show placement of the closure device;

FIG. 16 is a perspective view of an alternate embodiment of the closure device of the present invention having four clip legs to retain the covering member; and FIG. 17 is a perspective view of another alternate embodiment of the present invention wherein the clip legs are placed on the distal side of the defect and the covering member is placed on the proximal side.

DETAILED DESCRIPTION OF PREFERRED EMBODIMENTS

Referring now in detail to the drawings where like reference numerals identify similar or like components throughout the several views, the present invention provides a closure device for closing the patent foramen ovale (PFO) and a delivery system for placement of the closure device. With initial reference to FIGS. 1-3 which show the closure device in the deployed (placement) configuration, the closure device 10 includes a clip component 12 and a covering member or patch 20. The covering member (patch) 20 is expandable within the atrium, on a distal side of the defect, and is retained in position by legs 14 and 16 of clip 12 which engage the tissue on the proximal side of the defect. The closure device further includes a wire 30 having an annular shape as shown in FIG. 2 to extend around at least an inside perimeter of the covering member 20 to form it into a disc or ring shape. The wire 30 is configured to expand the covering member 20 to a diameter of at least equal to and preferably greater than, the size of the defect to provide a patch on the distal side of the PFO. The expanded member 20 thereby blocks the opening to prevent blood flow from the left atrium to the right atrium.

With reference to FIGS. 4-6, the delivery system for the closure device includes a catheter or delivery tube 50, a pusher 60 for advancing the patch 20 and attached clip 12 and a pusher (not shown) for advancing the wire 30 into the patch. Pusher 60 has an axial lumen 64 to slidably receive the wire pusher. The pusher can in one embodiment (not shown) be removably attached to the patch and detachable to separate the pusher after the patch 20 has been properly placed at the desired surgical site. One way of achieving this detachable connection is by providing a screw thread (not shown) on the distal end of the pusher. Such attachment is shown in co-pending patent application Ser. No. 60/674,321, filed Apr. 22, 2005, the entire contents of which are incorporated herein by reference. The screw thread would thread into a support connected to a proximal end of the patch 20. Axial movement of the pusher would advance the patch 20; rotational movement of the pusher would unscrew it from the support. Other ways to removably connect the pusher to the patch are also contemplated.

The clip 12 functions as a retaining member and preferably includes two clip legs 14, 16 extending distally from patch 20, preferably in opposite directions. The legs 14, 16 can be attached to the patch by adhesive or other means. These retaining legs 14, 16 are dimensioned and configured to engage tissue adjacent the defect on the proximal side P (see e.g., FIG. 14) to help retain the closure device 10 in position. Preferably the clip legs 14, 16 are composed of shape memory material, such as Nitinol, with an austenitic shape memorized position illustrated in FIGS. 1 and 3. Materials other than Nitinol or shape memory are also contemplated. The clip legs can be formed of a single wire or separate wires or material. The clip legs 14, 16 are maintained in a substantially straightened softer martensitic configuration within the catheter 50 for delivery as shown in FIG. 5. Cold saline can be injected during delivery to maintain the legs 14, 16 in this martensitic condition to facilitate exit from the distal opening 52 at the distal end portion 54 of catheter 50. When legs 14, 16 exit the delivery tube 50, they are warmed by body temperature and move radially in different (e.g., opposite) directions toward their illustrated curved position as shown for example in FIG. 3. The extent to which the clip legs return to their memorized position will depend on the thickness and resistance of the tissue. As an alternative to two clip (retention) legs, a single clip leg or more than two clip legs could be provided. FIG. 16 illustrates by way of example four clip legs. In this alternate embodiment, the four clips legs 114, 116, 118, and 120, are spaced about 90 degrees apart and provided to retain the patch 122. The clip legs in these various embodiments could include penetrating tips to engage and penetrate the tissue or blunt tips to just engage the tissue. Blunt tips, e.g., tips 14a, 16a, 114a, 116a, 118a, and 120a, are shown in the illustrated embodiments.

The patch 20 can be composed of a variety of materials, such as PFTE, polyethylene, swine intestinal submucosa, endothelium and/or other native tissues such as vein, artery, umbilical, or pericardium as either an allograft or xenograft. The patch could be coated with a hydrophilic, heparin, antiplatelet or anti-thrombogenic coating. The patch 20 is in the collapsed configuration within catheter 50 for delivery as shown in FIG. 5 or further rolled as in FIG. 7; it is expanded by the wire 30 to the configuration of FIGS. 1-3.

The wire 30 is preferably composed of shape memory material, such as Nitinol, with an austenitic annular shaped memorized position illustrated in FIGS. 2 and 3. However, materials other than Nitinol are also contemplated.

When advanced from the delivery tube 50, the wire 30 is warmed by body temperature and moves from its delivery configuration of FIG. 5 to its memorized annular configuration within patch 20. That is, wire 30 is maintained in a softer martensitic configuration within the catheter or patch to reduce its profile (overall transverse dimension) for delivery. Cold saline can be injected during delivery to maintain the wire 30 in this martensitic condition to facilitate exit from the distal opening 52 at the distal end portion 54 of catheter 50. In the memorized position, the wire assumes an annular shape along the inside periphery of the patch 20. As shown it extends more than 360 degrees as portion 32 of wire 30 overlaps an annular portion of the wire (see FIG. 3).

The embodiment of FIGS. 7 and 8 differs from the embodiment of FIGS. 5 and 6 in that the expanding wire 30' is fed into the patch 20 in situ. That is, instead of delivering the patch with the wire already inside as in FIGS. 5 and 6, the wire is advanced into the patch in a separate step after the patch is released to the distal side of the defect. This is explained in detail below in conjunction with the method of placement.

The method of placement of the closure device of the present invention will now be described. The method described is for the embodiment of FIGS. 7 and 8 where the wire is advanced in situ. Note, in the embodiment of FIGS. 5 and 6, the wire 30 is contained within the patch 20 during delivery so upon ejection of the patch 20 from delivery tube 50, the patch 20 automatically expands. This avoids the additional step of advancing the wire (the step of FIG. 12). However, it slightly increases the overall delivery profile since the patch cannot collapse to the same degree because of the wire contained therein. In the embodiment of FIGS. 7 and 8, the wire 30' is contained in an elongated substantially straight delivery configuration to provide a smaller profile.

The delivery catheter 50 is inserted through an introducer sheath in the femoral vein and advanced to access the atria as shown in FIG. 9. For insertion, the patch 20, clip 12 and wire 30 are all in the collapsed position. That is, shown in FIG. 7, the clip legs 14, 16 are in a substantially straight position. The wire 30' is also in a substantially straight position and patch 20 is collapsed and could be partially rolled. This provides for a reduced profile insertion configuration. FIG. 10 shows a close-up view of the catheter distal end positioned adjacent the septal opening.

In the first step, pusher 60 is advanced distally, (e.g., by a handle (not shown) or other mechanism) at a proximal end of the catheter 50 in the direction of arrow F of FIG. 10. Distal advancement of pusher 60 advances the closure device from the catheter 50 as the distal end 62 of pusher 60 abuts patch 20. That is, advancement of the pusher in the direction of arrow F of FIG. 10 advances patch 20 from catheter 50 into the right atrium (see FIG. 11) on the distal side D of the defect. The patch 20 remains at this point in the collapsed configuration. Once fully ejected, it still remains in an unexpanded configuration.

Next, the wire pusher (not shown) is advanced distally in the direction of arrow E of FIG. 12 so engagement of the distal end of the wire pusher with the proximal end 31 of wire 30' will force wire 30' into the patch 20. As the wire 30' exits the catheter 50 and enters the patch 20 within the right atrium, it is warmed by body temperature and moves toward its shape memorized overlapping annular configuration. This annular configuration expands patch 20 into a disk shape or a ring shape. FIG. 13 illustrates the patch 20 in an expanded configuration due to the movement of the wire to its memorized configuration.

Note that in a preferred embodiment, the wire pusher can have a radiopaque marker which can align with the radiopaque marker 56 on the catheter 50. This will provide a visual indication to the user that the pusher has completed its travel and the wire 30' has been inserted as the two markers align and provide a relatively large solid area for imaging. This will occur on full advancement of the wire pusher. A radiopaque marker can also be provided at the base of legs 14, 16 adjacent the patch 20 for imaging. Alignment of the radiopaque members is described in application Ser. No. 60/674,321 referenced above.

After full insertion of the wire 30' into the patch 20, the pusher 60 along with the catheter 50 are withdrawn, releasing the clip legs 12, 14 from the catheter to the proximal side P of the opening to enable movement toward their memorized curved position as they are warmed by body temperature. In their curved position, they grasp tissue on the proximal side P of the defect to retain patch 20 in place to cover the opening to prevent blood flow therethrough. Withdrawal of the catheter 50 leaves the closure device 10 in place as shown in FIGS. 13, 14 and 15. As shown, the patch 20 will be positioned at the distal side opening to block the opening (defect) in the atrium to prevent blood flow from the left atrium (proximal side) to the right atrium through the defect. As shown, the legs have free ends uncovered to directly engage tissue.

It should be appreciated that in an alternate embodiment, the patch is placed on the proximal side of the defect and the legs are placed on the distal side. This is shown in FIG. 17, wherein patch 220 is placed on the proximal side P of the defect and the retaining legs 214, 216 are placed on the distal side D.

While the above description contains many specifics, those specifics should not be construed as limitations on the scope of the disclosure, but merely as exemplifications of preferred embodiments thereof. For example, the patch could be used to close other openings in the body. Those skilled in the art will envision many other possible variations that are within the scope and spirit of the disclosure as defined by the claims appended hereto.

What is claimed is:

1. A device for closing a septal defect of a patient having a first side and a second side, the device comprising:

a fluid blocking covering patch having a proximal surface and a distal surface and a first non-expanded configuration for delivery and a second larger expanded configuration for placement on the first side of the defect, the covering patch composed of a first material having a dimension at least equal to a size of the defect to cover the defect and block fluid flow, the proximal surface of the patch engaging tissue on the first side of the defect the distal surface of the patch out of engagement with tissue;

a support unattached to the covering patch and advanceable into the covering patch at the proximal end of the covering patch, the covering patch movable from the first configuration to the expanded configuration in response to receipt of the support therein; and first and second retaining legs extending proximally of the proximal surface of the patch to contact tissue on the second side of the defect to retain the covering patch, the first and second legs composed of a second material different than the first material and having a first reduced profile configuration for delivery and a second configuration for placement on the second side of the defect, the first and second retaining legs having free ends uncovered to directly engage tissue.

2. The device of claim 1, wherein the support is composed of shape memory material.

3. The device of claim 1, wherein the support is in the form of a wire movable from a delivery configuration to a second configuration, the support being substantially ring-shaped in the second configuration.

4. The device of claim 3, wherein the support is composed of shape memory material.

5. The device of claim 1, wherein the first and second retaining legs are composed of shape memory material.

6. The device of claim 1, wherein the covering patch is placed on the distal side of the defect and the first and second retaining legs are placed on the proximal side of the defect.

7. The device of claim 1, wherein the legs curve radially outwardly to engage tissue on the second side of the defect.

8. The device of claim 7, wherein the two retaining legs are composed of shape memory material.

9. The device of claim 1, further comprising third and fourth legs extending in different directions and in the second configuration, the four legs curve radially outwardly to engage tissue on the second side of the defect.

10. The device of claim 1, wherein the covering member is substantially disc-shaped.

11. The device of claim 1, the support includes a wire expandable to an annular configuration.

12. The device of claim 11, wherein the wire is initially retained in an elongated configuration and is delivered to the covering member after the covering member is positioned on the first side of the defect.

13. The device of claim 1, wherein the support comprises a wire which is positioned circumferentially within the covering member.

14. The device of claim 1, wherein the covering member has a ring shape in the second configuration.

15. The device of claim 1, wherein the support is advanced into the covering member and moves to an annular configuration within the covering member to move the covering member to the second configuration, the covering member being disk shaped in the second configuration.

* * * * *